United States Patent [19]

Mosher

[11] Patent Number: 4,705,751
[45] Date of Patent: Nov. 10, 1987

[54] PROCESS FOR PREPARATION OF MULTIMERIC PLASMA FIBRONECTIN

[75] Inventor: Deane F. Mosher, Madison, Wis.

[73] Assignee: Wisconsin Alumni Research Foundation, Madison, Wis.

[21] Appl. No.: 566,215

[22] Filed: Dec. 28, 1983

[51] Int. Cl.[4] ..................... A61K 37/02; C07K 15/14; C12N 5/00; C12P 21/00
[52] U.S. Cl. .................................. 435/68; 435/240.3; 424/101; 514/8; 530/380
[58] Field of Search ........................ 435/240, 241, 68; 424/101, 177; 260/112 R, 112 B; 514/8; 530/380

[56] References Cited

PUBLICATIONS

Oberley et al.; "The Effect of the Dimeric and Multimeric Forms of Fibronectin on the Adhesion and Growth of Primary Glomerular Cells", *Experimental Cell Research* 145, 1983, pp. 265–276.

Mosher et al.; "Cross-linking of Collagen and Fibronectin by Factor XIIIa"; *J. Biol. Chem.*, vol. 255, No. 3, Feb. 10, 1980, pp. 1181–1188.

Mosher et al.; "In Vitro Formation of Disulfide-bonded Fibronectin Multimers"; *J. Biol. Chem.* vol. 258, pp. 6595–6601 (1983).

Smith et al.; "Immunological Identification of Two Sulfhydral-containing Fragments of Human Plasma Fibronectin"; *J. Biol. Chem.* vol. 257, 5831–5838 (1982).

Morrison and Boyd, "Organic Chemistry", (Allyn and Bacon Eds. 1974) p. 1173.

Primary Examiner—Thomas G. Wiseman
Assistant Examiner—Elizabeth C. Weiman
Attorney, Agent, or Firm—David J. Houser

[57] ABSTRACT

A method for preparation of multimeric fibronectin. Dimeric fibronectin is treated with guanidine. The dimeric fibronectin so treated is then incubated to allow multimeric fibronectin to form therefrom.

21 Claims, 1 Drawing Figure

PROCESS FOR PREPARATION OF MULTIMERIC PLASMA FIBRONECTIN

This invention was made with Government support under NIH Grants Nos. 5R01 HL 24885-02, 5R01 HL 24885-03, 2R01 HL 21644-04, 5R01 HL 21644-05 and 5R01 HL 21644-06 awarded by the Department of Health and Human Services. The Government has certain rights in this invention.

TECHNICAL FIELD

This invention relates generally to the modification of biological proteins, and, more specifically, to the conversion of naturally occurring, predominantly dimeric fibronectin to another form similar to an alternative, naturally occurring, multimeric form of fibronectin.

BACKGROUND OF THE ART

Fibronectin is a glycoprotein that occur naturally in various contexts within animal organisms. Fibronectin occurs as a soluble protein in blood and certain other body fluids and may be isolated from blood plasma. In fact, a form of fibriconectin found in human blood plasma is a major by-product of the isolation of blood coagulation Factor VIII, also called antihemophilic factor. Antihemophilic factor is currently isolated from human blood plasma in considerable quantities for the treatment and control of the symptoms of hemophilia. Consequently, blood plasma fibronectin produced as a by-product is relatively plentiful. Having no particular use, it is generally discarded.

Fibronectin also occurs as an insoluble protein in tissue stroma. Fibronectin bonds to collagen, fibrin, heparin, heparan sulfate, eukaryotic cells, and gram positive bacteria. It is probably an opsonin, and it is also a substrate for blood coagulation Factor $XIII_a$, also called plasma tranglutaminase.

Fibronectin occurs in subunits that are bound together in more than one way. In its soluble form, as found in plasma, fibronectin occurs primarily in a dimeric form. The insoluble forms of fibronectin are predominatly multimeric. While dimeric fibronectin is easily isolated from blood plasma, multimeric fibronectin is extremely difficult to isolate. Attempts have been made to isolate multimeric fibronectin from the surfaces of cells on which it is found. A solution of urea is mixed with the cell culture and, after agitation, the solution is separated from the cells. The protein content of the solution is then isolated. This process is unsatisfactory in many ways. It is very expensive. Furthermore, the resulting multimeric fibronectin ix mixed with unpredictable quantities of other materials incidentally stripped from the cell surface with the fibronectin. Consequently, multimeric cell surface fibronectin so produced is a poorly defined material that may vary in content from preparation to preparation. Because of the difficulty and relatively unsatisfactory nature of the preparation, the isolation of mutimeric fibronectin is rarely attempted commercially, and then primarily with cell cultures that may be conveniently managed. Commonly, only multimeric fibronectin isolated from chick embryo fibroblasts and from human foreskin fibroblasts is commercially available. Preparations of multimeric fibronectin are many times more expensive than preparations of dimeric, plasma fibronectin.

Multimeric fibronectin is a growth stimulant for cell cultures, including such diverse types of cells as kidney cells and nerve cells. Dimeric fibronectin isolated from blood plasma is also a growth stimulant, but multimeric fibronectin is much more potent. At present, multimeric fibronectin is not available in sufficient quantities or at a price economical enough to be employed in commercial cell culturing processes. Furthermore, the multimeric fibronectin that is available, being a poorly defined substance for the reasons noted above, is unsuitable even for experimental uses in situations in which reproducibility of processes is vital or in which it is necessary to be able precisely to define the contents of reagents used.

SUMMARY OF THE INVENTION

The invention is summarized in that a method for preparing multimeric fibronectin includes the steps of treating dimeric fibronectin having free sulfhydryl groups with guanidine to at least partially expose the free sulfhydryl groups. The dimeric fibronectin so treated is then incubated to allow multimeric fibronectin to form therefrom.

A primary object of the invention is to provide for the preparation of multimeric fibronectin from a source other than cell surface fibronectin.

A second object of the invention is to provide multimeric fibronectin derived from a plentiful and inexpensive source so as to allow the production of relatively large quantities of multimeric fibronectin at a reduced cost compared to current methods.

A further object of the invention is to provide a multimeric fibronectin preparation that is chemically defined and does not contain significant incidental materials having biological effects that are either unpredictable or unquantifiable.

Yet another object of the invention is to provide a method for preparing multimeric fibronectin that can be readily used to prepare such fibronectin from plasma fibronectin produced by a wide variety of animal species.

Other objects and advantages of the invention will be apparent from the following detailed description setting forth the preferred embodiment of the invention.

DETAILED DESCRIPTION OF THE PREFERRED EMBODIMENT

Figure 1:
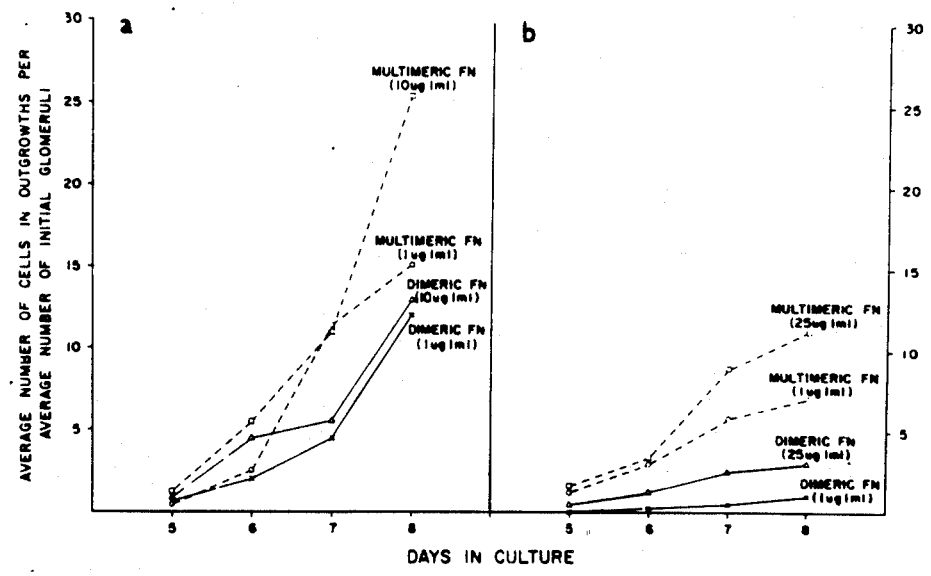
FIG. 1 is a graph relating to Example 4 and showing the effects of multimeric and dimeric fibronectin on the growth of cultured cells.

Plasma fibronectin and fibronectin synthesized and secreted by cultured cells consists primarily of 400 to 500 kilodalton disulfide-bonded dimers. The dimers are composed of similar, 200 to 250 kilodalton subunits. These subunits are linked together by interchain disulfide bridges located near the carboxyl termini of the subunits. In addition to the interchain disulfide bridges, there are also a number of intrachain disulfide bonds, which create small homologous loops. In addition to the intra and interchain disulfide bonds, there are probably two free sulfhydryls for each subunit within the dimer.

On the subunits of soluble plasma fibronectin, the free sulfhydryls normally exist in a reduced state. Presumable the free sulfhydryls are so oriented or otherwise affected by the other parts of the protein that they are not exposed to many potential chemical interactions. Thus, these free sulfhydryls generally do not react with sulfhydryl reagents in physiologic saline. Insoluble fibronectin in cell culture exists primarily as disulfide-bonded mutimers. Multimer formation may occur as a consequence of the oxidation of the free sulfhydryls of the dimers. This is suggested by the fact that modification of soluble firbonectin not containing multimers with N-ethylmaleimide at an alkaline pH so as to block the otherwise free sulfhydryls prevents the fibronectin from binding to the cell layer. See D. D. Wagner and R. O. Hynes, *J. Biol. Chem.* 254, pp. 6746–6754 (1979).

The method of the invention to convert soluble, primarily dimeric fibronectin into a predominantly multimeric configuration first requires that fibronectin in the predominantly dimeric form be isolated from a convenient source. Dimeric fibronectin preferably is isolated from blood plasma, whether human fibronectin is desired or that of other species. The dimeric fibronectin is then so treated as to cuse disulfide bonded multimers to form, presumably by exposing the free sulfhydryls of the dimer and the subsequent formation of disulfide bonds by oxidation of the free sulfhydryls. It should be stressed that the exact nature of the bonding either between fibronectin subunits or between dimers to form multimers is not precisely known. The comments herein about the chemical relationship between fibronectin subunits, dimers, and both naturally occurring and artificially made multimers and about the chemical reactions involved are somewhat speculative. They are intended only to express the inventors's best understanding of the invention and not to limit it.

The preferred process of isolating or purifying predominantly dimeric human fibronectin uses as a source thereof the protein side fractions remaining as by-products of the production of human blood coagulation Factor VIII, mentioned above. If not intended for immediate utilization, the side fractions may be frozen into a paste for storage. To be used subsequently, the frozen past must be dissolved, preferably in a buffered saline solution of an approximately neutral pH. Any material remaining undissolved in removed mechanically. Fibrinogen is then precipitated from the solution by heating and is removed. The fibronectin in the remaining solution is purified by application of the solution to a selected adsorptive column, such as a column of DEAE cellulose or gelatin agarose. After such application, fibronectin can be eluted from the column, precipitated by dialysis against ammonium sulfate, and dissolved in and dialyzed against buffered saline of approximately neutral pH. The fibronectin so purified may be used immediately or be snap frozen for storage at −70° C. Aside from the step in which fibrinogen is precipitated by heating, the fibronectin being purified is kept at or near physiologic conditions throughout the purification process.

The fibronectin so purified is predominantly dimeric. This material is then subjected to the method of the invention for producing multimeric fibronectin. The predominantly dimeric fibronectin is treated by subjecting the fibronectin to a "denaturing agent," hereby defined as a substance or combination of substances having the effect of tending to expose sulfhydryl groups on the subunits of fibronectin. It is believed that such denaturing agents tend at least transiently to alter the configuration of the fibronectin. Preferably this is accomplished by treating the fibronectin with guanidine in aqueous solution. Guanidine concentrations greater than approximately 1M are required to expose sulfhydryl groups, with increasing number of sulfhydryl groups being exposed as the concentration of guanidine is increased to a maximum of approximately 3M. No additional reactive sulfhydryl groups are exposed at guanidine concentrations greater than 3M. Upon sufficient exposure of sulfhydryl groups, multimers being to form.

The denaturing agent then may be removed from the fibronectin by dialysis against buffered saline. When this is done, a granular precipitate forms on the sides of the dialysis bag. The granules coalesce with time to form a thick, stringly precipitate enriched in the larger multimers of fibronectin. The precipitate readily dissolves in saline buffered at approximatey pH 11. Alternatively, multimeric fibronectin may be dialyzed directly from guanidine into buffered saline at pH 11 with no intervening step of precipitation. Multimeric fibronectin dissolved in saline buffered at pH 11 precipitates when diluted in or dialyzed against saline buffered at approximately pH 7.4. In contrast, dimeric fibronectin that has not been subjected to the guanidine treatment disclosed above is soluble both in saline at pH 11 and saline buffered at or near pH 7.4.

As is noted above, the exact chemical configuration of the multimeric fibronectin produced by the process of the invention is not known. However, there is evidence that suggests that the availability of free sulfhydryl groups is important to the method of the invention and that the formation of multimers consumes a considerable number of the free sulfhydryl groups, presumably in the formation of disulfide bonds. Thus, dimeric fibronectin in which free sulfhydryls are blocked by alkylation with N-ethylmaleimide or iodoacetamine does not form disulfide-bonded multimers in guanidine-containing solutions. Dimeric fibronectin in saline buffered at pH 7.4 has essentially no exposed free sulfhydryl groups and, except as qualified below, does not spontaneously form multimers. The same dimeric fibronectin in a 3M solution of guanidine has approximately 1.5 exposed free sulfhydryl groups per 200 kilodalton subunit. As is disclosed above, such dimers combine to form fibronectin multimers. Once formed, the multimers have 45% fewer free sulfhydryl groups than the fibronectin dimers. The presence of free sulfhydryl groups may be detected quantitatively with 5,5'-dithio-bis (2-nitrobenzoic acid) or 2,2'-dipyridyl disulfide, as is described in D. E. Smith, D. F. Mosher, R. B. Johnson, and L. T. Furcht, *J. Biol. Chem.* 257, pp. 5831–5838 (1982).

A variety of substances that are known to interact with fibronectin do not serve to expose the sulfhydryl groups of the dimers and do not cause multimer formation. These substances include collagen type III, alpha-1(I)-CB7 (a fibronectin-binding collagen fragment), fibrinogen, heparin, hyaluronic acid, calcium ion, EDTA, deoxycholate, and methylamine. The effects of these potential modifiers of the dimer were tested by the inventor by treating dimeric fibronectin with each potential modifier and then assaying for the presence of exposed free sulfhydryl groups by the method noted above. Each potential modifier was incubated with dimeric fibronectin in physiologic saline for 60 minutes at 22° C., except that methylamine was incubated at 37° C. In each case, exposed free sulfhydryl groups were found not to be present in significantly increased amounts.

Urea is known to expose sulfhydryl groups in dimeric fibronectin. However, treatment of dimeric fibronectin with urea does not lead to formation of significant amounts of multimeric fibronectin. That fact and the results of the tests with substances known to interact with fibronectin referred to above rendered especially surprising that guanidine can be used successfully to so expose the sulfhydryl groups of dimeric fibronectin and allow formation of multimeric fibronectin.

The multimeric fibronectin produced in accord with the invention is characterized in part by the method of its making. In addition, it is substantially biologically pure. It can be further characterized by comparision with dimeric plasma fibronectin. Thus, the multimeric fibronectin of the invention held in saline buffered at pH 7.4 is readily cross-linked by blood coagulation Factor XIII$_a$ under conditions in which little cross linking of dimeric fibronectin occurs. Multimers of the invention also exhibit the ability to bind to gelatin-agarose after dilution in saline buffered at pH 7.4 to a final concentration of 500 μg/ml, at which dilution precipitation does not occur. Under standardized conditions, 79% of the multimer binds to gelatin agarose as compared to 77% binding for dimeric fibronectin that has been previously dialyzed into saline buffered at pH 11.

Multimers and dimers are digested differently by trypsin. Analysis of the fragments remaining after treatment with trypsin was made by the inventor, utilizing conventioanl gel electrophoresis as described by G. F-L. Ames, *J. Biol. Chem.* 249, pp. 634–644 (1974); and D. F. Mosher, M. J. Doyle and E. A. Jaffe, *J. Cell Biol.* 93, pp. 343-348 (1982). Fragments resulting from trypsin digestion of fibronectin dimers include fragments of 180, 135, 71, and 31 kilodaltons. See D. E. Smith, D. F. Mosher, R. B. Johnson, and L. T. Furcht, *J. Biol. Chem.* 257, pp. 5831–5838 (1982), and D. E. Smith and L. T. Furcht, *J. Biol. Chem* 257, pp. 6518-6523 (1982). The amounts of these fragments produced upon trypsin digestion of the multimers of the invention, as opposed to dimers, are much decreased, as perceived both by protein staining and immunofluorescent staining. Several new fragments occur in the digestion of multimers, the fragments having apparent sizes (non-reduced/reduced) of 54/57 and 36/37 kilodaltons, as detected by protein staining. Nonreduced fragments of 70 and 32 kilodaltons may be detected by immunofluorescence. In addition, digestion of the multimers of the invention, as opposed to dimers, produces increased amounts of small fragments detected by immunoflurescence in nonreduced digests, the fragments having a size less than 20 kilodaltons.

Cyanide cleavage of conventional plasma fibronectin dimer and the multimers of the invention results in patterns in sodium dodecyl sulfate-polyacrylamide electrophoresis gel similar to those described by D. D. Wagner and R. O. Hynes, *J. Biol. Chem.* 255, pp. 4304–4312 (1980). However, the yield, as determined by densitometry, of the principal 156 kilodalton cleavage component ws 5.4% in the preparation of the multimers as compared to 12.7% in the preparation of dimer. Multimer cleavage products were not detected in the 20–50 kilodalton region of the gels, even after silver staining.

It is known that both plasma fibronectin and the fibronectin synthesized in cell culture form disulfide-bonded multimers upon incorporation into the extracellular matrix. However, it is not known how free sulfhydryls of dimeric fibronectin are exposed in the cell layer to participate in the formation of disulfide-bonded multimers, if indeed they do at all. As is disclosed above, a variety of substances, at least some of which are present in vivo, are known to bind to dimeric fibronectin but do not expose free sulfhydryl groups in vitro. It is possible that small fraction of free sulfhydryls are exposed spontaneously at any one time, so that if the fibronectin molecules in the cell layer are aligned optimally, multimer formation could occur without conformational or other changes to further expose free sulfhydryls. Alternatively, exposure may be facilitated by the binding of fibronectin to two or more substances simultaneously or to a substance not yet tested for its ability to expose the free sulfhydryls of dimeric fibronectin. The free sulfhydryls of fibronectin synthesized by cells may be exposed in a manner different from those present in plasma fibronectin. Furthermore, disulfide bonded multimer formation in the cell layer may not involve free sulfhydryls at all. Instead, the observed disulfide bonds may result from exchange of existing disulfides. Consequently, it is not likely that the multimeric fibronectin produced by the process of the invention is identical to naturally occurring fibronectin multimer found in the cell layer. Indeed, it is almost inevitable that a variety of differences exist. However, the multimeric fibronectin produced by the method disclosed above has been shown in cell growth studies to be a significantly more potent growth stimulant than naturally occurring dimeric fibronectin.

Trace amounts of multimeric fibronectin were found to be present in primarily dimeric, untreated plasma fibronectin examined by the inventor. It is not known what degree of correspondence there may be between the mechanism of formation, the structure, and other qualities of the multimeric fibronectin so found and that produced by the method of the invention. The trace amounts may result from surface interactions with the containers and equipment with which the plasma has been in contact and not be found at all in undisturbed plasma. And again, formation of the multimer found in trace quantities may not involve free sulfhydryls at all, resulting instead from the exchange of existing disulfides. In any event, these amounts are not formed by a mechanism that leads to progressively larger amounts of the multimer or that causes it to form in concentrations sufficient to be isolated by the method disclosed above.

The following are specific examples embodying the method of the invention, disclosed above:

EXAMPLE 1

Purification of Fibronectin

In the examples, tris(hydroxymethyl)aminomethane shall be referred to as "TRIS". Cyclohexylaminopropane sulfonic acid shall be referred to as "CAPS".

Fibronectin was purified from fibronectin- and fibrinogen-rich protein side fractions of human blood coagulation Factor VIII production. The protein side fractions were available as a frozen paste, provided by Dr. Mike Hrinda, Revlon Health Care Group, Tuckahoe, New York. Approximately 80 g of the frozen paste was dissolved for 120 minutes at 22° C. with constant stirring in 600 ml of 0.01M TRIS, 0.4M sodium chloride, pH 7.4. At the end of that time, any material remaining undissolved was removed by centrifugation. The solution was subjected to heating at 56° C. for 3 minutes, whereupon fibrinogen precipitated. The fibrinogen was removed by centrifugation.

The resulting supernatant was dialyzed against 4 l of 0.01M TRIS, 0.01M sodium chloride, pH 7.4, and then applied to a 6.5×13.5cm column of DEAE cellulose.

Prior to application of the supernatant, the DEAE cellulose had been equilibrated with 0.01M TRIS, 0.07M sodium chloride, p. 7.4. After the pass-through peak was eluted, a 2 1 gradient solution of 0.07M to 0.3M sodium chloride in 0.01 TRIS, pH 7.4, was applied to remove the bound fibronectin. The fibronectin was precipitated by dialysis against a solution of ammonium sulfate having a concentration of 20% by weight. The precipitated fibronectin was then dissolved in and dialyzed against 0.01M TRIS, 0.15M sodium chloride, pH 7.4. The fibronectin solution was snap frozen for storage in portions of selected sizes at concentrations of 15 to 20mg/ml. The portions were stored at −70° C. Aside from the step in which fibrinogen was precipitated by heating at 56° C. for 3 minutes and the step of snap freezing the fibronectin at the end of purification, the fibronectin was kept at near physiological conditions throughout the purification.

When the purified fibronectin was analyzed by polyacrylamide gel electrophoresis after reduction, 99% of the protein was in a band of 200 kilodalton. The 200 kilodalton band could be resolved into two closely spaced bands of equal intensity if only 1 to 2 μg of protein were analyzed. These results indicate that the fibronectin had a purity of approximately 99%. Analysis of purified fibronectin by electrophoresis without reduction, analysis of whole human plasma by the same technique, and gel electrophoresis of purified fibronectin without reduction followed by gel electrophoresis after reduction produced results suggesting that a molecule of 40 to 60 kilodalton is disulfide-linked to a small proportion of fibronectin molecules. See D. F. Mosher and R. B. Johnson, "Disulfide-bonded Fibronectin Multimers." *J. Biol. Chem* 258, 6595–6601 (1983).

EXAMPLE 2

Alternative Method of Purification of Fibronectin

Fibronectin was purified from a sample of the fibronectin- and fibrinogen-rich protein side fractions of human blood coagulation Factor VIII, referred to in Example 1, above, using the same steps and substantially the same quantities, with the substitution of a column of gelatin agarose for the column of DEAE cellulose specified in Example 1. Fibronectin bound to the column of gelatin agarose was eluted with 1M sodium bromide at pH 5.0. The purified fibronectin was comparable in all ways, including degree of purity, to that of Example 1.

EXAMPLE 3

Conversion of Dimeric Fibronectin to Multimeric Fibronectin

Predominantly dimeric fibronectin purified from protein side fractions of human blood coagulation Factor VIII in accord with Example 1 was selected for use. A solution was prepared of the purified fibronectin having a concentration of 7mg/ml. This solution was incubated in 3M guanidine. Disulfide-bonded multimers formed in the solution in a time and temperature dependent manner. After the reaction was deemed to be sufficiently complete, guanidine was removed by dialysis against TRIS-buffered saline, pH 7.4. A granular precipitate formed on the dialysis bag. Over time, the granules coalesced to form a thick, stringly precipitate. After dialysis at 22° C., the precipitate contained approximately 30% of the fibronectin when the initial fibronectin concentration in the bag was greater than 1.5mg/ml. The precipitate was found to be enriched in the larger multimers. After dialysis at 4° C., the precipitate contained approximately 75% of the fibronectin when the initial concentration in the bag had been 1.5mg/ml. The precipitate was observed to dissolve readily in CAPS-fubbered saline, pH 11. Fibronectin dialyzed directly from guanidine into CAPS-buffered saline did not precipitate. Without regard to whether it had originally been precipitated to be redissolved in CAPS-buffered saline or if it had been directly dialyzed into CAPS-buffered saline, multimeric fibronectin dissolved in CAPS-buffered saline precipitated when diluted in or dialyzed against TRIS-buffered saline, pH 7.4 Because of the purity of the dimeric fibronectin used, the multimeric fibronectin produced therefrom was substantially biologically pure.

EXAMPLE 4

Stimulation of Cell Growth

Glomeruli were isolatd from young adult guinea pigs by the nylon screening technique described by Oberley et al., *Invest. Cel. Pathol.* 2, p. P27 (1979). They were then cultured in Waymouth's media, MB 752/1 (obtained from Gibco Laboratories. Grand Island, N.Y.) The media was supplemented with 1% sodium pyruvate, 1% non-essential amino acides, and penicillin-streptomcycin (100 units/ml). In addition, the media was supplemented with insulin (5mg/ml), transferrin (5mg/ml), selenium (5ng/ml) (all prepared from insulin, transferrin, selenium premix obtained from Collaborative REsearch, Inc., Lexington, Massachusetts), Dimeric or multimeric fibronectin were added in concentrations ranging from 0.1 to 25 mg/ml). Cell growth was then monitored. For direct visual comparison of cell growth, cells were photographed with a Ziess bright-field microscope using Panatomic X film. The results reported herein were obtained early in the glomerular culture before the appearance of mesangial cells.

In comparisons of the average number of cells observed each day with the average number of initial glomeruli, it was apparent that glomerular cells grew better in multimeric than in dimeric fibronectin at fibronectin concentrations of 1 to 10 μg/ml. See FIG. 1(a). This stimulating effect of multimeric fibronectin was even more apparent at a concentration of 25 μg/ml. See FIG. 1(b). At these concentrations, cell growth was two to three times better in multimeric than in dimeric fibronectin after eight days of culture. Experiments were also run in which glomerular cells were cultured in a comparable media in which the insulin, transferrin, and selenium were replaced by glycylhistidyl lysine. It was found that multimeric fibronectin also stimulated growth better than dimeric fibronectin in such media, thus showing that preferential growth stimulation by multimeric fibronectin is not dependent upon the presence of insulin, transferrin, and selenium.

It is to be understood that the examples given above record only particular instances and examples of the method of the invention. The present invention is not limited to the particular reagents, steps, or methods disclosed herein. Instead, it embraces all such modified forms thereof as come within the scope of the following claims.

What is claimed is:

1. A method for preparing multimeric fibronectin comprising the step of treating dimeric fibronectin with guanidine by preparing an aqueous solution of dimeric fibronectin and guanidine wherein the concentration of quanadine is at least 1M, whereby multimeric fibronectin is formed within the solution.

2. The method of claim 1 wherein the step of treating fibronectin with guanidine further comprises preparing an aqueous solution including guanidine in a concentration of at least 2M.

3. The method of claim 1 further comprising the step of removing unreacted guanidine from the solution of dimeric fibronectin and guanidine after formation of multimeric fibronectin.

4. The method of claim 3 wherein the step of removing unreacted guanidine comprises removal of guanidine by dialysis.

5. The method of claim 1 comprising, before the step of treating dimeric fibronectin with guanidine, the step of purifying dimeric fibronectin from blood plasma.

6. The method of claim 5 where the multimeric fibronectin is human multimeric fibronectin and wherein the step of purifying dimeric fibronectin from blood plasma comprises utilizing the protein side fractions remaining as by-products of the production of human blood coagulation Factor VIII by dissolving such side fractions in water and heating them to precipitate fibrinogen, removing the fibrinogen so precipitated, and purifying the fibronectin remaining in solution by affinity chromatography.

7. The method of claim 6 wherein the step of purifying the fibronectin by affinity chromatography comprises applying the solution containing fibronectin to a column of DEAE cellulose, eluting the pass-through peak, the removing the fibronectin bound to the column by applying thereto a gradient solution of increasingly concentrated sodium chloride buffered at a substantially neutral pH.

8. The method of claim 6 wherein the step of purifying the fibronectin by affinity chromatography comprises applying the solution containing fibronectin to a column of gelatin agarose, eluting the pass-through peak, and eluting the fibronectin from the column with a solution of sodium bromide at a pH less than 7.

9. The method of claim 8 wherein the step of eluting the fibronectin bound to the gelatin agarose column includes eluting the fibronectin with a solution of approximately 1M sodium bromide at approximately pH 5.0.

10. Multimeric fibronectin prepared by the method of claim 1 and capable of stimulating cell growth when included in effective amounts in cell culture media.

11. Multimeric fibronectin prepared by the method of claim 5 and capable of stimulating cell growth when included in effective amounts in cell culture media.

12. A method for the preparation of multimeric fibronectin comprising the step of preparing an aqueous solution of guanidine in a concentration of at least 1M and dimeric fibronectin isolated from blood plasma, whereupon multimeric fibronectin forms from the dimeric fibronectin.

13. The method of claim 12 wherein the step of preparing the aqueous solution of guanidine comprises preparing the aqueous solution of quanidine in a concentration of at least 2M.

14. The method of claim 12 further comprising, following the step of incubating the solution of guanidine and fibronectin, the step of removing guanidine from the incubated solution of quanidine and fibronectin.

15. A method for preparing multimeric human fibronectin comprising the steps of:
(a) purifying dimeric fibronectin from the protein side fractions of blood plasma remaining as by-products of the production of human blood coagulation Factor VIII by heating such side fractions dissolved in water to precipitate the fibrinogen, removing the fibrinogen so precipitated, purifying the dimeric fibronectin remaining in solution by affinity chromatography, including the steps of desorbing and eluting the dimeric fibronectin from any adsorbent materials utilized for performing the affinity chromatography, precipitating the dissolved dimeric fibronectin by dialysis against ammonium sulfate, and dissolving the dimeric fibronectin in buffered saline of approximately neutral pH capable of dissolving the dimeric fibronectin; and
(b) adding guanidine to the dissolved dimeric fibronectin in amounts sufficient to achieve a concentration of guanidine of at least 2M, whereby multimeric fibronectin forms from the dimeric fibronectin.

16. Multimeric fibronectin prepared by the method of claim 12 and capable of stimulating cell growth when included in effective amounts in cell culture medial.

17. A substantially pure preparation of multimeric fibronectin.

18. The substantially pure preparation of multimeric fibronectin of claim 17 prepared in vitro from dimeric blood plasma fibronectin.

19. A method of stimulating cell growth comprising the step of exposing cells being cultured in a culture media whose growth is to be stimulated to a substantially pure preparation of multimeric fibronectin by incusion of the multimeric fibronectin in the culture media.

20. A method of stimulating cell growth comprising the steps of:
(a) treating dimeric fibronectin with guanidine by preparing an aqueous solution of dimeric fibronectin and guanidine wherein the concentration of guanidine is at least 1M, whereupon multimeric fibronectin forms in the aqueous solution; and
(b) exposing cells being cultured in a culture media whose growth is to be stimulated to the multimeric fibronectin by inclusion of the multimeric fibronectin in the culture media in amounts effective to stimulate cell growth.

21. The method of claim 20 comprising, before the step of treating dimeric fibronectin with guanidine, the further step of purifying dimeric fibronectin from blood plasma.

* * * * *

UNITED STATES PATENT OFFICE
CERTIFICATE OF CORRECTION Page 1 of 2

Patent No. 4,705,751    Dated Nov. 10, 1987

Inventor(s) Deane F. Mosher

It is certified that error appears in the above-identified patent and that said Letters Patent are hereby corrected as shown below:

Please Amend

In Column 1, line 14, change "bilogical" to -- biological --.

In Column 1, line 20, change "occur" to -- occurs --.

In Column 1, line 24, change "fibriconectin" to -- fibronectin --.

In Column 1, line 52, change "ix" to -- is --.

In Column 1, line 59, change "mutimeric" to -- multimeric --.

In Column 2, line 65, change "able" to -- ably --.

In Column 3, line 3, change "mutimers" to -- multimers --.

In Column 3, line 18, change "cuse" to -- cause --.

In Column 3, line 38, change "past" to -- paste --.

In Column 3, line 68, change "number" to -- numbers --.

In Column 4, line 5, change "being" to -- begin --.

In Column 4, line 11, change "stringly" to -- stringy --.

In Column 4, line 32, change "iodoacetamine" to -- iodoacetamide --.

In Column 5, line 46, change "immunoflurescence" to -- immunofluorescence --.

In Column 6, line 2, change "that small" to -- that a small --.

In Column 7, line 63, change "stringly" to -- stringy --.

UNITED STATES PATENT OFFICE
CERTIFICATE OF CORRECTION

Patent No. 4,705,751         Dated Nov. 10, 1987

Inventor(s) Deane F. Mosher

It is certified that error appears in the above-identified patent and that said Letters Patent are hereby corrected as shown below:

In Column 8, line 31, change "REsearch," to -- Research --.

Signed and Sealed this

Twenty-third Day of August, 1988

Attest:

DONALD J. QUIGG

*Attesting Officer*     *Commissioner of Patents and Trademarks*